United States Patent [19]
Landskron et al.

[11] Patent Number: 4,838,873
[45] Date of Patent: Jun. 13, 1989

[54] APPARATUS FOR INTRODUCING LIQUIDS AND/OR ELONGATED ELEMENTS INTO A BODY CAVITY

[75] Inventors: Jürgen Landskron, Bebra; Jörn Zahn, Kassel; Harald Heckmann, Lohfelden; Georg Mohr, Wildeck-Honebach, all of Fed. Rep. of Germany

[73] Assignee: Intermedicat GmbH, Emmenbrucke, Switzerland

[21] Appl. No.: 198,591

[22] Filed: May 23, 1988

Related U.S. Application Data

[63] Continuation of Ser. No. 897,619, Aug. 18, 1986, abandoned.

[30] Foreign Application Priority Data

Aug. 24, 1985 [DE] Fed. Rep. of Germany ....... 3530349

[51] Int. Cl.$^4$ ............................................. A61M 25/00
[52] U.S. Cl. ..................................... 604/283; 604/905
[58] Field of Search ................................ 604/164–170, 604/240, 243, 283, 905; 156/73.1; 285/242, 255

[56] References Cited

U.S. PATENT DOCUMENTS

| 3,469,579 | 9/1969 | Hubert | 604/283 |
| 3,728,184 | 4/1973 | Burke et al. | 156/73.1 |
| 3,802,433 | 4/1974 | Raven | 604/283 |
| 3,806,386 | 4/1974 | Burke et al. | 156/73.1 |
| 3,970,490 | 7/1976 | Raines et al. | 156/73.1 |
| 4,049,034 | 9/1977 | Vcelka et al. | 156/73.1 |
| 4,219,912 | 9/1980 | Adams | 156/73.1 |
| 4,391,029 | 7/1983 | Czuba et al. | 604/283 |
| 4,606,783 | 8/1986 | Guest | 156/73.1 |
| 4,650,529 | 3/1987 | Guest | 156/73.1 |

Primary Examiner—Dalton L. Truluck
Assistant Examiner—Denise Whelton
Attorney, Agent, or Firm—Spensley Horn Jubas & Lubitz

[57] ABSTRACT

The apparatus for medical purposes comprises a sleeve-type catheter hub (10) having a cylindrical longitudinal channel (11) and a flexible catheter capillary (24) which, through an orifice portion (11a) of the longitudinal channel (11) extends into an expanded intermediate section (11c) of the longitudinal channel (11). The catheter capillary (24) includes a thicker head portion (23) tightened in the expanded intermediate section (11c) of the longitudinal channel (11) by an annular shoulder (22) of a radial annular collar (20) which is formed by ultrasonic welding into the wall of the longitudinal channel (11). To obtain a stepless passage of the cylindrical channel (11), an adapter (18) with a conical passage (19) is joined by press fit to the annular collar (20). The catheter capillary (24) is firmly anchored. In addition, the conical passage (19) serves as an insertion aid for a probe or the like.

2 Claims, 2 Drawing Sheets

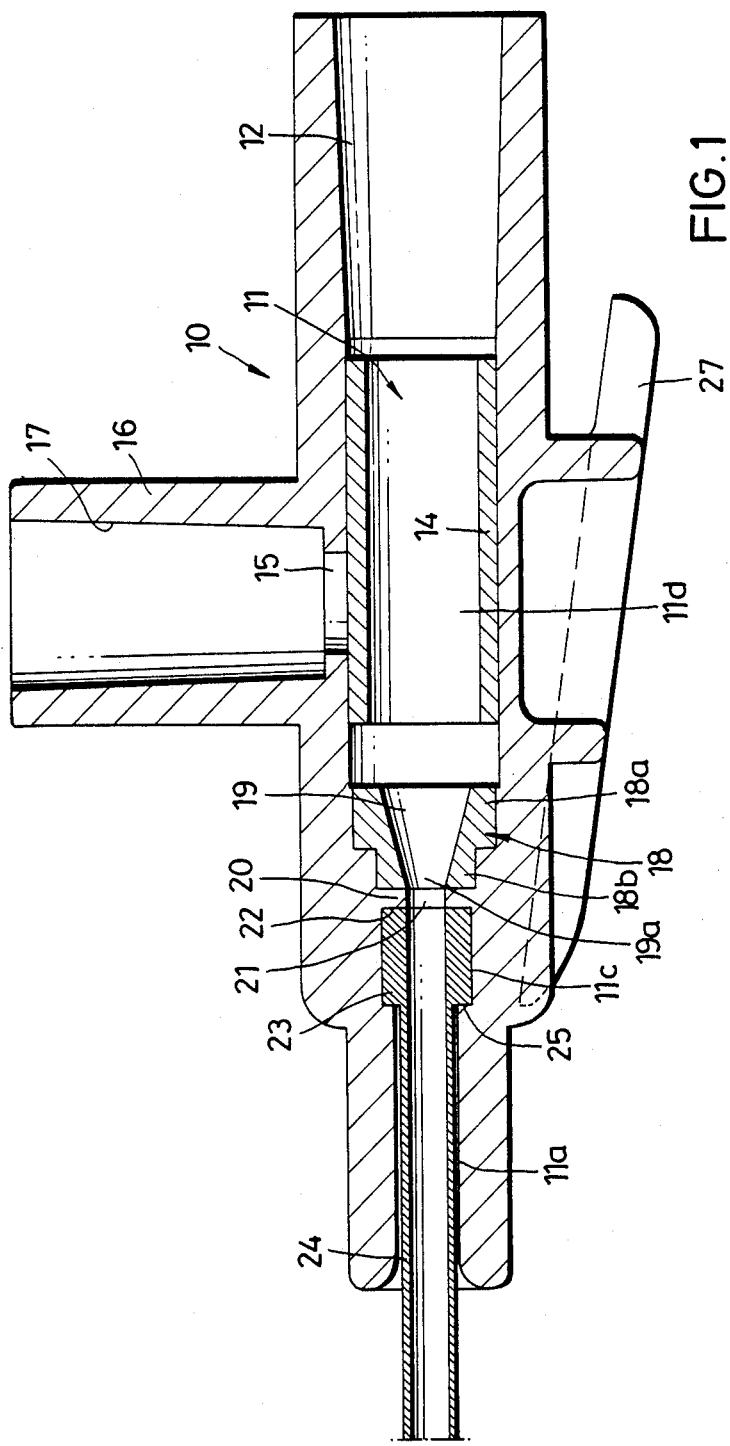

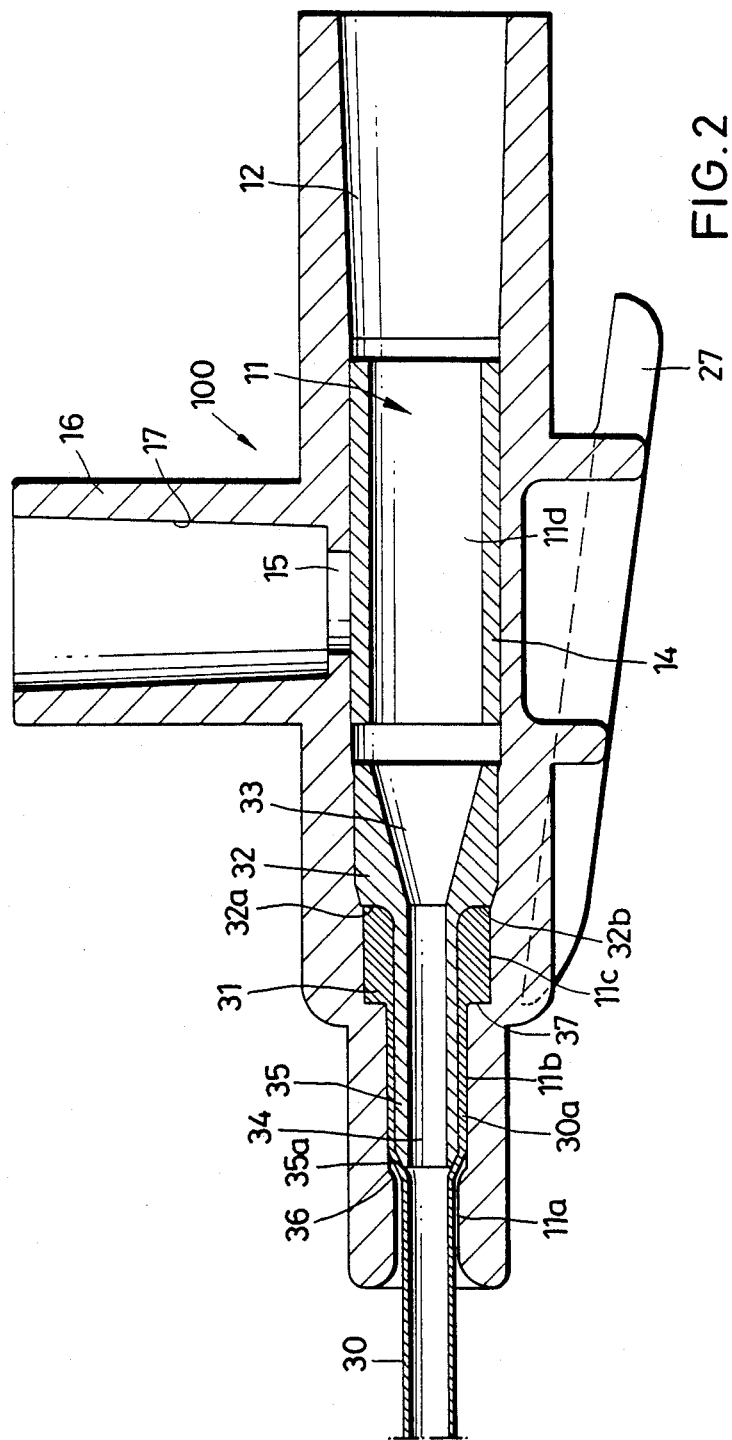

APPARATUS FOR INTRODUCING LIQUIDS AND/OR ELONGATED ELEMENTS INTO A BODY CAVITY

This is a continuation of application Ser. No. 897,619, filed on Aug. 18, 1986 now abandoned.

The invention relates to an apparatus for introducing liquids and/or elongated elements such as cannulae, mandrins, catheters and the like into a body cavity comprising a sleeve-type catheter hub including a cylindrical longitudinal channel and a flexible catheter capillary which, through an orifice portion of the longitudinal channel substantially adapted to its outer diameter extends into an enlarged intermediate section of the longitudinal channel whose diameter is superior to the external diameter of the catheter capillary and in which the latter is fixed by a fastener.

The connection between a catheter capillary and a catheter hub has to be undetachable to prevent the catheter capillary from getting off the catheter hub and from thus migrating into the body of a patient. It is particularly difficult to establish such a firm connection because, generally, catheter capillaries are made of polytetrafluoroethylene (PTFE) or of another plastic material having a low friction coefficient to avoid adhesion of blood particles thus excluding thrombus formation and the plastic material being hardly wettable so that injection moulding therearound with a thermoplast used as catheter hub material cannot be performed satisfactorily. Efforts have been made accordingly to establish a firm connection between catheter capillary and hub by using mechanically means.

It has been known to use to this effect cylindrical metal sleeves having an outer diameter superior to that of the inner diameter of the catheter capillary and expanding radially part of the catheter capillary extending into the longitudinal channel in the form of a hose having a constant wall thickness which is pressed against an expanded cylindrical wall portion of the longitudinal channel. In a known apparatus of this type (German laid-open Patent Application No. 19 34 287), both ends of the cylindrical metal sleeve are straightly cut off, its one end pressing the catheter capillary against a transition shoulder intermediate the two longitudinal channel sections of different diameters while its other end is provided with a catheter hub portion upset radially to the inside. The sleeve being made of metal and sharp-edged, there is the risk for the thin-walled catheter capillary stretched at the transition shoulder to be damaged if, during the upsetting of the catheter hub material, axial pressure is exerted on said sleeve. Due to the low friction coefficient of the catheter capillary material, a slipping of the smooth hose out of its clamped position between longitudinal channel wall and sleeve is not excluded.

Another known apparatus (German Patent No. 22 44 618) also provides a metal sleeve expanding radially a catheter capillary section of a constant wall thickness. Further, the inner sleeve end is fitted with a flange disposed with a clearance in an enlarged connecting chamber of the longitudinal channel between an annular adapter and a snap attachment. Again, the risk of damage for the catheter capillary is high at the transition shoulder intermediate longitudinal channel sections of different diameters where the blunt sleeve end may press against the catheter capillary to tear it through. Said risk is favored by the play of the flange in the connecting chamber because, during the insertion of an elongated element, increased axial pressures may be applied to the sleeve.

Moreover, due to the clearance in the connecting chamber, fluid may accumulate which, in case of a longer residence time of the device, for inst. of a short catheter, may endanger by its contamination the patient.

In another apparatus (US 3 454 006) also making use of a metal sleeve as a fastener whose blunt end presses the catheter hose against a transition shoulder intermediate longitudinal channel sections of various diameters, the inner end of the sleeve is provided with a conical flange which is upset into an inclined wall of the connecting chamber. In view of the very small dimensions of catheter capillary and sleeve, it is quite difficult to retain them against axial upsetting forces and to thus exclude damages at the transition shoulder during the upsetting of the catheter capillaries.

It is the object of the invention to improve the known devices so that a firm connection is established between catheter capillary and catheter hub without running an risk of damaging the catheter capillary by the fastener.

The problem is solved according to the invention in that the catheter capillary is provided with a thick head portion which is tightened in the expanded intermediate section of the longitudinal channel by an annular shoulder of a tension element.

As an advantage resulting from such a thick head portion of the catheter capillary in connection with a tension element, the latter may be fitted without applying to the catheter capillary forces detrimental thereto. The tension element only acts against the end face of the head portion of the catheter capillary to compress it somewhat axially whereby it is radially enlarged and its clamping in the expanded intermediate section of the longitudinal channel is intensified. The thin hose capillary remains unaffected by said events, and it will not be tensioned anywhere such as to tear or rip up. The thick head portion of the catheter capillary is a cylindrical part forming a collar around the catheter capillary end and being produced by deformation under heat action.

According to an advantageous embodiment of the invention, the tension element is a radial annular collar formed by ultrasonic welding into the wall of the longitudinal channel. The annular collar ensures the desired compression of the thick head portion which is retained in the enlarged intermediate section of the longitudinal channel. In case of elements of such small dimensions, it is easier to apply a bead by ultrasonic welding than by upsetting. Further, there are no axial upsetting forces caused during upsetting and responsible for undesired deformations within the longitudinal channel of the catheter hub. The annular collar produced by ultrasonic welding is of a flat parallel-faced type.

If the apparatus is used for liquid infusions, for removing body secretion or the like, the shape of the longitudinal channel at the inner end of the thick head portion of the catheter capillary is substantially meaningless. However, if an elongated element, e.g. a cannula, a mandrin, a catheter or the like is to be inserted into the body cavity by means of the apparatus, the passage must not contain any rectangular step due to which the advance of the respective element will be stopped. It being difficult to form in the annular collar production by ultrasonic welding a conical channel profile, the invention provides an annular adapter having a conical passage which is clampingly pressed into the longitudinal channel and applied against the annular collar. From the patient-distal side of the catheter hub, the adapter is introduced into the longitudinal channel to be clamped in a section thereof fitted to it. The adapter may contain a number of axially successive sections of different outer diameters. By this means, material may be saved and the axially successive diameters of the longitudinal channel on both sides of the annular collar may be more or less equal, thus facilitating the formation by ultrasonic welding of an opening in the annular collar which opening substantially corresponds to the inner diameter of the plastic capillary and to the smaller opening of the adapter.

According to an advantageous embodiment of the invention, the tension element consists of a cylindrical plastic bushing adapted by press fit into the longitudinal channel, said plastic bushing replacing the ulstrasonic welding operation and facilitating the assembly of the device while ensuring a safe coherence between catheter hub and catheter capillary. The plastic bushing presses axially against the thick head portion of the catheter capillary to effect its reliable clamping without entailing damages of the thin-walled catheter capillary. The assembly is simple and the friction contact between catheter hub of plastic and plastic bushing is excellent, so that its fixation at the desired point in the longitudinal channel is safeguarded.

The plastic bushing may include a coaxial cylindrical sleeve having an outer diameter larger than the inner diameter of the catheter capillary. Said sleeve may extend at least into the thick head portion of the catheter capillary and press it against the wall of the enlarged intermediate section of the longitudinal channel. Thus, the cylindrical sleeve forms an additional retentive force acting on the head portion of the catheter capillary by pressing it radially to the outside so that its outer surface is pressed more intensely against the wall of the longitudinal channel. It is possible to elongate the sleeve as far as into the catheter capillary. Its free end is advantageously inclined externally thus excluding squeezing effects at a transition shoulder between sections of different diameters of the longitudinal channel. The plastic bushing may comprise a conical passage extending coaxial to the longitudinal channel and being tapered towards the catheter capillary, said conical passage serving as an insertion aid for elongated elements. Since it is formed in the plastic bushing serving as a tension element, the design, production and assembly of the device is simplified.

Embodiments of the invention are shown schematically in the drawing in which

FIG. 1 is a longitudinal section of an embodiment of the apparatus for introducing liquids and/or elongated elements, and FIG. 2 shows a second embodiment of such an apparatus.

The apparatus consists of a sleeve-type catheter hub 10 having a cylindrical longitudinal channel 11 divided into a number of coaxially successive sections and the patient-distal end of which is joined by an inner cone 12 to receive an outer cone of the connecting piece of an infusion hose, an injection syringe or the like. Section 11d of the longitudinal channel 11 situated next to inner cone 12 houses a coaxially provided valve hose 14 against the wall of which ends the opening 15 of a piece 16 with inner cone 17 which serves for injecting liquids into the longitudinal channel 11. Piece 16 may be closed by a non-illustrated cover. Spaced from the blunt end of the valve hose 14, a cylindrical annular adapter 18 disposed in section 11d of the longitudinal channel 11 is mounted by press fit. The adapter 18 made of plastic contains a section 18a and a section 18b coaxially joined thereto and of a smaller diameter. Its passage 19 is conical and tapered towards the patient-proximal end of the device. The flat end side of adapter 18 abuts against a flat face of a radial annular collar 20 fitted by ultrasonic welding prior to the mounting of adapter 18, the annular collar 20 surrounding a central opening 21 whose diameter substantially corresponds to the opening 19a of the tapered end of passage 19 thus ensuring a stepless transition between openings 19a, 21. The radial annular collar 20 rests against a flat annular face 22 of a circular cylindrical, thick head portion 23 of a catheter capillary 24 and presses its opposite annular face projecting rectangularly from the catheter capillary 24 against an adapted annular shoulder 25 in the longitudinal channel wall. Together with the confronting annular face 22 of the annular collar 20 and the wall of the longitudinal channel 11, the annular shoulder 25 forms an enlarged intermediate section 11c in which the thick head portion 23 is fixed as an anchorage for the catheter capillary 24 which anchorage is radially pressed apart by axial force. The catheter capillary 24 with head portion 23 consists of polytetrafluoroethylene or of a similar fluorcarbon plastic having a low friction coefficient. The hose-shaped portion of the catheter capillary 24 joined to the head portion 23 extends straightly and loosely through the orifice section 11a of the longitudinal channel 11 whose diameter substantially corresponds to the outer diameter of the catheter capillary 24. Damages of the thin wall of the catheter capillary 24 due to fixation elements deforming it are excluded. By its cylindrical thick head portion 23, the catheter capillary 24 is firmly retained in the enlarged intermediate section 11c of the longitudinal channel 11, the radial annular collar 20 intensifying this effect by axially pressing against the thicker head portion 23 which is somewhat pressed apart radially and firmly anchored in the enlarged intermediate section 11c.

Since the conicity of passage 19 imparts to the longitudinal channel 11 of the catheter hub 10 an inclined inlet passing over steplessly through opening 21 into the equally dimensioned passage of the catheter capillary 24, the apparatus may not be employed only for infusing liquids, but it also well lends itself to inserting elongated elements such as cannulae, mandrins, catheters etc. into a body cavity. The underside of the catheter hub 10 is provided with flaps 27 directed transversely to its longitudinal axis and used to fix the catheter hub 10 on the patient's skin for inst. by means of an adhesive plaster.

The embodiment of FIG. 2 shows a catheter hub 100 being also of the sleeve type design provided with a laterally projecting piece 16 with inner cone 17 which, by an opening 15 and a flexible valve hose 14 gives access to the cylindrical longitudinal channel 11 of the catheter hub 100. The patient-distal end of the longitudinal channel 11 is joined by an inner cone 12 serving to receive a corresponding outer cone of a connecting piece. This embodiment also includes flaps 27 provided at the underside of the catheter hub 100.

Also in this case, one end of the catheter capillary 30 is provided with a thick circular cylindrical head portion 31 serving as an anchorage element. On the other hand, the radial annular collar 20 of FIG. 1 does not exist, but a cylindrical plastic bushing 32 is forcibly fitted into part of the longitudinal channel 11 whose diameter substantially corresponds to the diameter in the range of the valve hose 14. The outside of the plastic bushing 32 is of a circular cylindrical shape, while its inside contains a conical passage 33 continued by a cylindrical passage 34 in a coaxial, circular cylindrical sleeve 35 formed to one end of the plastic bushing 32. The cylindrical sleeve 35 projects through the thick head portion 31 to extend over some distance inside the catheter capillary 30. In this region, the longitudinal channel 11 is divided into three coaxially successive sections, namely the orifice section 11a of a diameter substantially corresponding to the outer diameter of the catheter capillary 30, the enlarged section 11b into which projects sleeve 35 and the enlarged intermediate section 11c receiving the thicker head portion 31 of the catheter capillary 30. The transition 36 of the wall from the channel section 11a to the channel section 11b is of a somewhat inclined design, the inclination corresponding to an inclination 35a on the outer periphery of the end of sleeve 35. The wall transition 37 from section 11b to section 11c is of a rectangular shape.

With its shoulder 32a passing over into sleeve 35 via a concave round-off portion 32b, the cylindrical plastic bushing 32 presses against the end face of the thicker head portion 31 to axially compress it with a resultant radial enlargement of said head portion which is pressed against the wall of the intermediate section 11c. Additionally, in the range of the longitudinal channel section 11b, the head portion 31 as well as part 30a of the catheter capillary 30 are pressed to the outside thus improving the retention effect for the catheter capillary 30. In this embodiment, the retaining force for the catheter capillary 30 is excellent due to the plastic bushing 32 contributing to the improved clamping retention effect by the radial enlargement of the thick head portion 31 as a result of axial pressure, and due to the sleeve 35 contributing to such improvement by the radial expansion. At the same time, the thin wall of the catheter capillary 30 cannot be damaged because at the transition 36 from the longitudinal channel section 11b to the orifice section 11a, the end of sleeve 35 does not exert any contact pressure on the catheter capillary 30. There is only a tensionless guiding of the orifice section 11a of a smaller diameter to section 11b of a larger diameter. The retention force is exerted predominantly in the range of the thick head portion 31, while the thin wall of the catheter capillary 30 is kept free of detrimental forces.

What is claimed is:

1. Apparatus for introducing liquids and/or elongated elements such as cannulae, mandrins, catheters and the like into a body cavity, comprising:

a catheter hub having a substantially cylindrical, longitudinal channel therethrough, said catheter hub defining an elongated orifice portion of said longitudinal channel, a catheter capillary entending with loose fit into the elongated orifice portion of said longitudinal channel, an intermediate section of said longitudinal channel having a diameter greater than said orifice portion of said longitudinal channel, an internal stepped shoulder located where the intermediate section of said longitudinal channel meets the orifice portion of said longitudinal channel, said catheter capillary having a thick head portion situated within said intermediate section, said thick head portion having mutually parallel first and second annular plane faces, said thick head portion having a central opening, the relative distance between said mutually parallel first and second annular plane faces of said thick head portion being less than the length of said elongated orifice portion of said longitudinal channel, said first annular plane face abutting against said internal stepped shoulder, a radial annular collar formed by ultrasonic welding into the wall of the longitudinal channel, said annular collar having two mutually parallel, substantially flat surfaces extending normal to the longitudinal axis of the longitudinal channel, said second annular plane face of said thick head portion abutting against one of said substantially flat surfaces of said annular collar, said annular collar acting against substantially all of said second annular plane face of said thick head portion to axially compress and radially enlarge and clamp said thick head portion in said intermediate section of said longitudinal channel said annular collar defining a central opening adjacent said central opening of said thick head portion and having a diameter substantially equal to said central opening of said thick head portion, whereby a substantially stepless transition between said central opening of said thick head portion and said central opening of said annular collar is provided, and whereby said thick head portion is axially limited by said internal stepped shoulder and one of said substantially flat surfaces of said annular collar.

2. apparatus according to claim 1, wherein an annular adapter having a concial passage is situated in the longitudinal channel and abuts against the annular collar.

* * * * *